(12) United States Patent
Wallukat et al.

(10) Patent No.: US 7,745,139 B1
(45) Date of Patent: Jun. 29, 2010

(54) PEPTIDES OF THE AT₁ RECEPTOR AND THEIR USES

(75) Inventors: Gerd Wallukat, Berlin (DE); Volker Homuth, Schönow (DE); Friedrich Luft, Schwanebeck (DE)

(73) Assignee: Max-Delbrück-Centrum für Molekulare Medizin (DE)

( * ) Notice: Subject to any disclaimer, the term of this patent is extended or adjusted under 35 U.S.C. 154(b) by 0 days.

(21) Appl. No.: 09/868,967

(22) PCT Filed: Dec. 22, 1999

(86) PCT No.: PCT/DE99/04112

§ 371 (c)(1),
(2), (4) Date: Jan. 18, 2002

(87) PCT Pub. No.: WO00/39154

PCT Pub. Date: Jul. 6, 2000

(30) Foreign Application Priority Data

Dec. 24, 1998 (DE) .............................. 198 60 320
Nov. 11, 1999 (DE) .............................. 199 54 305

(51) Int. Cl.
*G01N 33/53* (2006.01)
*C07K 4/00* (2006.01)
*C07K 4/12* (2006.01)
*C07K 16/28* (2006.01)

(52) U.S. Cl. .................... 435/7.1; 530/300; 530/388.22

(58) Field of Classification Search ........................ None
See application file for complete search history.

(56) References Cited

FOREIGN PATENT DOCUMENTS

DE 19826442 A1 12/1999
WO 94/25482 A1 11/1994

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Pettit et al. (1998). The development of site-specific drug-delivery systems for protein and peptide biopharmaceuticals. Trends in Biotechnology. 16: 343-349.*
V. Homuth, et al.; "Characterization of Agonistic Antibodies against the Angiotensin AT₁ Receptor in Patients with Preeclampsia and HELLP Syndrome"; Kidney Blood Press Res; 1998, vol. 21; p. 358; Summary only.
S. Holzsch et al.; "The Pathophysiological Background of a Sustained Blood Pressure Reduction after Seriall Water Immersion"; Kidney Blood Press Res; 1998, vol. 21; p. 358; Summary only.
N. Hubner, et al.; Elevated Blood Pressure in Congenic Animals Carrying Chromosome 1 Alleles from the Stroke Prone Spontaneously Hypertensive Rat (SHRSP$_{HD}$); Kidney Blood Press Res; 1998, vol. 21; p. 358; Summary only.
Fu Michael LX et al.:"localization of angiotensin II receptors (ATI) in the heart with anti-peptide antibodies showing a positive chronotropic effect", abstract No. 232600, Chemical Abstracts, Columbus, Ohio, US, vol. 130, No. 18. May 3, 1999 & Recept. channels, 6(2), 99-111, 1998, XP002140152.
Popkov, Mikhail et al.:"Multidrug-resistance drug-binding peptides generated by using a phage display library" in Chemical Abstracts, abstract No. 240905, vol. 128, No. 20, May 18, 1998, Columbus, Ohio, US & Eur. J. Biochem., 251(1/2), pp. 155-163, 1998, XP002140153.
Schneider, G. et al.:"Peptide design by artificial neural networks and computer-based evolutionary search" in Proceedings of the National Academy of Sciences of USA, vol. 95, Issue 13, pp. 12179-12184, Oct. 13, 1998.

* cited by examiner

*Primary Examiner*—Christine J Saoud
*Assistant Examiner*—Jon M Lockard
(74) *Attorney, Agent, or Firm*—Joyce V. Natzmer; Pequignot + Myers

(57) ABSTRACT

Disclosed are peptides of the AT₁ receptor and their use for eliminating specifically binding, cell-physiologically active, pathological antibodies in preeclampsia and malign hypertension. The peptides may, for example, be used for the diagnosis of preeclampsia. Peptides having the sequence AFHYESQ (SEQ ID NO: 1), AVHYQSN (SEQ ID NO: 2), SHFYQTR (SEQ ID NO: 3), GYYFDTN (SEQ ID NO: 4) or ENTNIT (SEQ ID NO: 5) are preferred.

12 Claims, 2 Drawing Sheets

PEPTIDES OF THE AT$_1$ RECEPTOR AND THEIR USES

Figure 1:
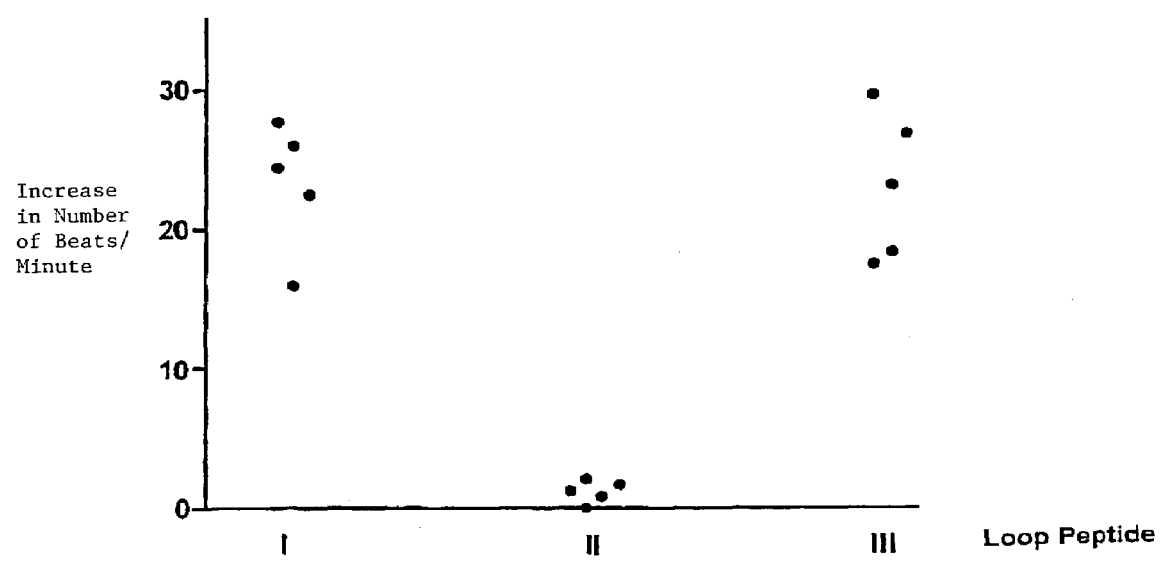
Figure 2:
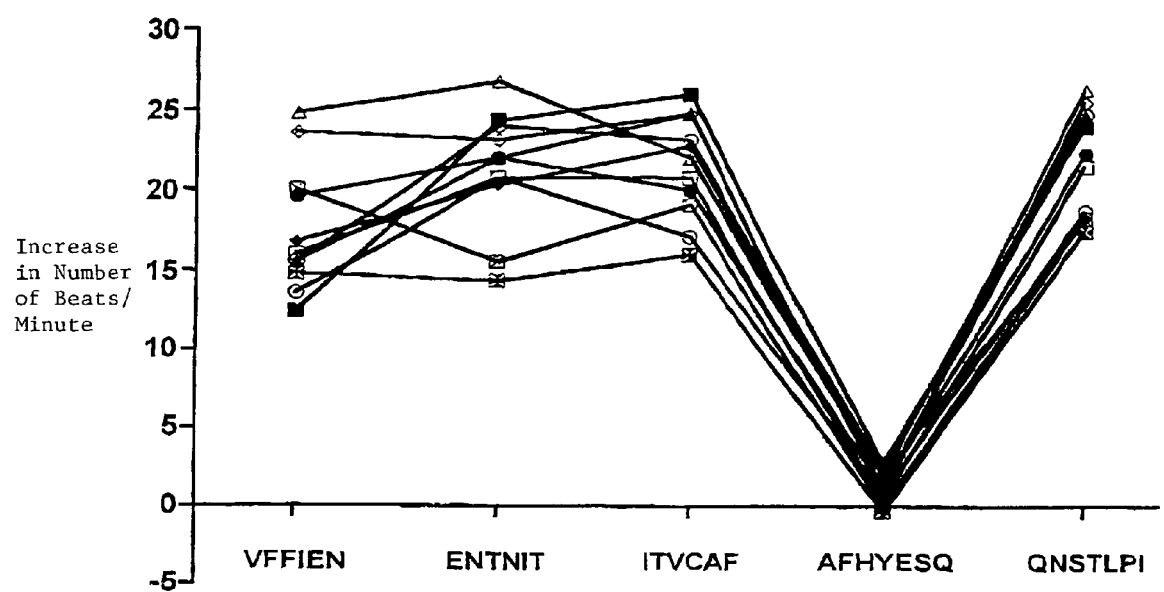

The invention relates to peptides of the AT$_1$ receptor and their use and subsequent products in antigenic and immunogenic agents and test kits, in particular for the elimination of specifically binding, cell-physiologically active, pathological antibodies in preeclampsia and for their diagnostic proof. In addition, the invention relates to a process for the proof of anti-AT$_1$ receptor antibodies in biological fluids.

The immune system is an essential component part of all animal life. In mammals, it is particularly used as a defence of micro-organisms, for tissue regeneration and for destruction of tumour cells. In classical immunology, a distinction is made between a cellular and a humoral immune defence. This means two distinguishable systems which nevertheless cooperate with one another, all told portraying the immune system.

There exist a series of diseases which are termed as auto-immune diseases. In such diseases, the immune system in the persons involved frequently works against itself. The predominantly cell-mediated auto-immune diseases include Multiple Sclerosis and Type I diabetes. A second groups is formed by the antibody-mediated auto-immune diseases. For example, this includes rheumatism or also the less frequent auto-immune diseases such as myasthenia gravis or lupus erymathematodes.

The pathogenesis of most auto-immune diseases is unknown. There are various hypotheses and models of how to explain the origin of auto-immune diseases. For example, one explanatory model portrays the antigenic/molecular mimicry. In this, it is presupposed that micro-organisms, e.g. viruses or parasites, equip themselves with certain molecules which are not recognised by the host's own immune system and avoid it. However, if they are recognised as being external and anti-bodies are induced and produced against them, these antibodies also recognise similar body-inherent structures.

Part of the nature of auto-immune diseases and auto-antibodies is that they bind onto body-inherent cells and tissue. In this, either the cellular immune system and the complementary system are activated, thus triggering pathogenic reactions in the tissue in situ—e.g. chronic inflammations—, or there is a pathological dysfunction of the cells to which the auto-antibodies have bound.

A classic example of this is dilatative cardiomyopathy. In this auto-immune disease, the organism incorrectly forms auto-antibodies which bind to a defined epitope of the β1-adrenergic receptor. These auto-antibodies generate an increase in the pulsation rate in biological tests on rat cardiomyocytes in a cell culture (these cells have a practically identical β1-adrenergic receptor on the surface). We speak of a pharmaco-active effect of the auto-antibodies, similar to that of adrenaline.

Dilative cardiomyopathy is an auto-immune disease which, if not treated, leads to major impairment of the cardiac output by reduction of the pumping performance with a simultaneous expansion of the heart muscle tissue by infiltrates. But if the antibodies are removed from the blood in the early stages of the disease by blood-washing, there is a regeneration of the heart muscle in the course of a year and a drastic improvement of the heart muscle performance, almost reaching the figures for healthy people again.

Apparently, the regeneration of the heart muscle can thus be initiated by the elimination of the pathological antibodies from the blood's circulation—and that is all that happens in the removal of the overall immunoglobulin.

The situation in preeclampsia is similar.

Preeclampsia is a pregnancy-specific form of high pressure and is one of the most important causes of maternal mortality during pregnancy and in the course of birth. Preeclampsia has even greater importance for the fate of the fruit, i.e. it is responsible for prematurity, retardation of growth and peri-natal mortality.

Although a great deal of knowledge has been obtained in the past few years, the causes of this clinical picture have yet to be clarified. The only causal therapy is premature termination of the pregnancy. However, if the symptoms of the disease occur at an early stage, i.e. particularly before the 20$^{th}$ week of pregnancy, this is hardly compatible with a healthy survival of the child. On the other hand, each day of extension of a pregnancy can improve the child's chances of survival in this critical phase. The best preconditions for achieving this objective are provided by early recognition (diagnosis) of the development of a preeclampsia and monitoring and treatment methods on this basis (immunoglobulin adsorption)

Therefore, the task of the invention entailed finding substances which enable the proof of pathological antibodies in preeclampsia and malign hypertension and provide corresponding systems therefor. A further task entails enabling the elimination of such antibodies from the blood.

The invention is implemented according to the claims, the sub-claims being preferred variants.

The invention is based on first-time proof that patients with preeclampsia manifest specific antibodies against blood-pressure-effective angiotensin-AT$_1$-receptors. These antibodies did not occur in women with normal pregnancies, likewise not with pregnant women with chronic hypertension, i.e. hypertension independent of the pregnancy. The angiotensin-II-AT$_1$-receptor antibodies observed lead to an activation of the AT$_1$-receptor, which is probably also responsible for dangerous increases of blood pressure and an acute deterioration of the supply of blood to vital organs of mother and child.

In patients with this disease, an immunoglobulin fraction can be isolated from the plasma, containing auto-antibodies which bind onto the angiotensin-1 receptor and activate the cell via it. If peptides of the AT$_1$ receptor portraying the point of binding for the antibodies are added to the cell culture system—in vitro—, the pathological effect of the auto-antibodies can be annulled. Similar things are possible by using peptides with analog functions, preferably with the amino-acid sequence AFHYESQ (SEQ ID NO: 1), AVHYQSN (SEQ ID NO: 2), SHFYQTR (SEQ ID NO: 3), GYYFDTN (SEQ ID NO: 4), ENTNIT (SEQ ID NO: 5).

The surprising thing is that the same epitope structures eliminate the anti-bodies responsible for the pathological effect from the blood plasma of the patients when they are bound to a solid phase.

An essential part of the invention is thus the provision of amino-acid sequences in the form of peptides which recognise, bind and eliminate the pathological auto-antibodies from the plasma of patients with preeclampsia.

Serum samples of patients with preeclampsia contain auto-antibodies which are directed against the angiotensin-II-AT$_1$ receptor sub-type. In a bioassay, these antibodies develop a positively chronotropic effect. This effect is inhibited like that of angiotensin II by the sub-type-selective AT$_1$ receptor blocker Losastan. Alpha and beta-adrenergic antagonists and the AT$_2$ receptor blocker PD 123319 had no influence.

It was surprisingly established that the antibodies recognise an epitope on the second extra-cellular loop of the AT$_1$ receptor and that they can be neutralised and affinity-chromatographically cleaned with the help of peptides corresponding to this loop. The epitope is characterised by the amino-acid sequence AFHYESQ (SEQ ID NO: 1). Further, function-analog peptides with the amino-acid sequence AVHYQSN (SEQ ID NO: 2), SHFYQTR (SEQ ID NO: 3), GYYFDTN (SEQ ID NO: 4) or ENTNIT (SEQ ID NO: 5) are part of the scope of the invention.

Thus, the object of the invention is peptides containing the epitope of the AT1 receptor binding physiologically active auto-antibodies, preferably comprising 5 to 10 amino-acids and their variants, which can form a epitope and bind auto-antibodies occurring in preeclampsia.

Peptides partially or totally containing SEQ ID NO: 1 (AFHYESQ) are preferred.

The peptides are synthesised or produced in gene technology according to methods known per se by the set-up of the amino-acids.

Antibodies according to the invention aimed against the epitope of the $AT_1$ receptor are characterised by the fact that they recognise these peptides. Preferably, they recognise the peptide of SEQ ID NO: 1 (AFHYESQ) or its variants. Further antibodies recognise the peptides with the amino-acid sequence AVHYQSN (SEQ ID NO: 2), SHFYQTR (SEQ ID NO: 3), GYYFDTN (SEQ ID NO: 4) or ENTNIT (SEQ ID NO: 5). They are produced with methods known per se by immunisation of small mammals or immunisation of spleen cells in vitro with the peptides according to the invention.

The antibodies are used in various bio-assays, immunological detection systems and ELISA test systems.

Further, the invention relates to antigenic agents for detection of preeclampsia, containing at least one peptide according to the invention, preferably the peptide of SEQ ID NO: 1 (AFHYESQ), or also peptides with the amino-acid sequence AVHYQSN (SEQ ID NO: 2), SHFYQTR (SEQ ID NO: 3), GYYFDTN (SEQ ID NO: 4), ENTNIT (SEQ ID NO: 5). They react with the specific antibodies against blood-pressure-effective angiotensin-$AT_1$ receptors occurring in preeclampsia. If need be, the antigenic agents are bound to various carriers, such as activated sepharose, cellulose or polystyrene carriers.

A further use of the peptides according to the invention entails immunogenic agents. These contain at least one peptide, preferably the peptide of SEQ ID NO: 1 (AFHYESQ), or also peptides with the amino-acid sequence AVHYQSN (SEQ ID NO: 2), SHFYQTR (SEQ ID NO: 3), GYYFDTN (SEQ ID NO: 4), ENTNIT (SEQ ID NO: 5), which induce the production of antibodies capable of recognising auto-antigens in preeclampsia.

In addition, a test kit for detection of anti-$AT_1$ receptor antibodies to prove preeclampsia is provided by the invention.

The test kit entails
at least one peptide according to the invention, if need be bound to a solid phase
a buffer
a specific conjugate plus enzyme
a washing solution
the substrate solution for detection of the enzyme reaction and a stop solution
The bio-assay entails
spontaneously pulsing neo-natal cardiomyocytes in primary culture or
cardiomyocytes differentiated from undifferentiated embryonal stem cells
in one culture medium Thanks to the development of the new test kits on the basis of the peptides according to the invention, the proof of preeclampsia and assessments of the sequence can be done quickly and simply.

The invention further relates to a process of detection of anti-$AT_1$ receptor antibodies in biological fluids. The sample to be examined is put into contact with at least one peptide according to the invention or with a combination of these peptides with a carrier material under conditions permitting an antigen-antibody reaction. Detection is then done by means of chemical or physical methods known per se.

The anti-$AT_1$ receptor antibodies were detected in all serums of patients with preeclampsia examined up to now. The antibodies appear after the $20^{th}$ week of pregnancy and disappear relatively quickly after labour. The anti-$AT_1$ receptor antibodies were not detected in normal pregnancies or in pregnant sufferers from hypertension.

As the antibodies behave like the agonist angiotensin II in in vitro tests, these antibodies play a role in pathogenesis or preeclampsia. As they can be detected in all preeclampsia serums examined, they are of importance as diagnostic markers.

Cultivated neo-natal rat heart cells were used as a bioassay. These cells develop a rhythmic spontaneous pulsation and react to an angiotensin-II stimulation with an increase of the beat frequency.

Detection of these $AT_1$ receptor antibodies according to the invention is used both for early recognition of preeclampsia and also as a basis for new therapeutic methods.

Thus, the object of the invention is also therapeutic agents against preeclampsia containing these peptides, as the removal of the angiotensin-$AT_1$ receptor antibodies from maternal blood (for example by means of specific or inspecific immuno-adsorption) leads to an improvement of the clinical image or can at least prevent a progression, which is connected with a reduction of the maternal risk and in particular with a distinct improvement of the chances of the child surviving.

The specific immunoglobulin adsorption is done on a column on which there are peptides in which at least the antibody-binding sequence AFHYESQ (SEQ ID NO: 1) is contained (preferably containing the second extra-cellular loop of the $AT_1$ receptor or SEQ ID NO: 1.

The inspecific immunoglobulin adsorption is done on a column preferably containing sheep's or chicken's antibodies against the human immunoglobulin or protein A or $C1_q$.

With this adsorber, all the Ig of the blood plasma, also the auto-antibodies directed against the $AT_1$ receptor, are bound and eliminated, making use of a suitable apparatus known to experts.

The invention described with the example of preeclampsia can equally be used for some cases of malign hypertension in which an auto-antibody recognising the same epitope (the same sequence) is also found.

The invention is to be explained below in more detail with some examples of embodiments.

FIG. 1:

Effect of Loops I-III of the $AT_1$ Receptor on the Cell-Contracting Activity of the Auto-Antibodies (Contained in the γ-Globulin Fraction Isolated from the Serum of Preeclampsia Patients)

The γ-globulin fraction of the serum of preeclampsia patients increases the beat frequency of the heart muscle cells by 22±x beats per minute (fictive). If the γ-globulin fractions are pre-incubated with peptides portraying these parts of the $AT_1$ receptor corresponding to loops I-III and the antibodies are subsequently added to the cell test system, the loop II peptides inhibit the antibody effect on the cells.

FIG. 2:

Epitope Analysis of Loop II of the $AT_1$ Receptor—Effect of Amino-Acid Sequences from Loop II on the Auto-Antibody-Mediated Cell Stimulations The γ-globulin fraction of the serum of preeclampsia patients increases the beat frequency of the heart muscle cells. The amino acid sequence AFHYESQ from loop II inhibits the effect of the auto-antibodies, but not, on the other hand, the sequence areas from other parts of loop II.

3. Bioassay to Detect the Antibodies

To identify and characterise the $AT_1$ receptor antibodies, a sensitive bioassay was used. Spontaneously pulsing cardiomyocytes reacting to an angiotensin-II stimulation with an increase of the beat frequency were used. This positively chronotropic effect was blocked by the selective antagonist Losartan. The incubation of these cells with the anti-$AT_1$ receptor auto-antibody also led to an increase of the pulsation rate, which was stopped by Losartan. Further, this agonistic effect was neutralised by a peptide corresponding to the second extra-cellular loop of the $AT_1$ receptor. In order to identify the epitopes of the auto-antibodies on the second extra-cellular loops of the angiotensin II $AT_1$ receptor, an attempt was made to neutralise the anti-$AT_1$ receptor auto-antibodies with short overlapping peptides. It was seen that two epitopes existed on this extra-cellular loop of the $AT_1$ receptor of hypertension sufferers, these being in a position to annul the effect of the antibody. These were the epitopes ENTNIT and AFHYESQ. In preeclampsia patients, the agonistic effect of the antibodies achieved via the $AT_1$ receptor was only neutralised by the peptide AFHYESQ. This epitope has a special importance in this disease, as it was identified in all the patients examined. The function-analog peptides SHFYQTR and GYYFDTN were also in a position to neutralise the antibodies, Tab. I.

TABLE I

| Patient No. | Antibody + 1:40 | Patients' antibodies, pre-treated with peptide | | |
|---|---|---|---|---|
| | | AFHYESQ | SHFYQTR | GYYFDTN |
| 1 | 19.6 ± 1.90 | 1.2 ± 0.84 | 0.8 ± 1.16 | 2.4 ± 0.72 |
| 2 | 20.0 ± 1.90 | 1.6 ± 1.24 | 0.8 ± 0.80 | 2.8 ± 1.20 |

The invention claimed is:

1. A method for binding auto-antibodies comprising:
providing isolated peptides of an $AT_1$ receptor consisting essentially of at least one of amino acid sequences SEQ ID NO: 1, SEQ ID NO: 2, SEQ ID NO: 3 or SEQ ID NO: 4, wherein said peptides bind auto-antibodies occurring in patients with preeclampsia,
contacting said peptides in vitro with a blood sample from a patient suspected of having preeclampsia under conditions permitting binding of said auto-antibodies with said peptide, and
binding said auto-antibodies in said blood sample via said peptides, wherein preeclampsia is diagnosed via said binding.

2. The method of claim 1, wherein said peptides are soluble or bound to a solid phase and wherein the method comprises a direct or indirect detection of said auto-antibodies in the blood sample.

3. The method of claim 1, wherein the blood sample is plasma or serum sample.

4. The method of claim 1, wherein the peptides are bound to a solid phase and wherein the method further comprises neutralizing said auto-antibodies via said peptides.

5. The method of claim 4, wherein said blood sample is maternal blood.

6. The method of claim 4, wherein said solid phase is part of a column.

7. A method of binding auto-antibodies against the angiotensin $AT_1$ receptor in a blood sample in vitro comprising contacting an isolated peptide of the $AT_1$ receptor with a body fluid under conditions permitting binding of said auto-antibodies with said peptide, wherein the peptide consists essentially of the amino acid sequence of SEQ ID NO: 1, SEQ ID NO: 2, SEQ ID NO:3, or SEQ ID NO:4.

8. The method of claim 7, wherein the peptide consists essentially of the amino acid sequence of SEQ ID NO:1.

9. The method of claim 7, wherein said blood sample is maternal blood.

10. The method of claim 7, further comprising detecting said auto-antibodies in said blood sample.

11. The method of claim 7, wherein the blood sample is plasma or serum sample.

12. A method of binding auto-antibodies against the angiotensin $AT_1$ receptor in maternal blood in vitro comprising contacting an isolated peptide of the $AT_1$ receptor with the maternal blood under conditions permitting binding of said auto-antibodies with said peptide, wherein the Peptide consists essentially of the amino acid sequence of SEQ ID NO: 1.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: designed
      peptide of the AT1 receptor

<400> SEQUENCE: 1

Ala Phe His Tyr Glu Ser Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: designed
      peptide of the AT1 receptor

<400> SEQUENCE: 2

Ala Val His Tyr Gln Ser Asn
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: designed
      peptide of the AT1 receptor

<400> SEQUENCE: 3

Ser His Phe Tyr Gln Thr Arg
1               5

<210> SEQ ID NO 4
<211> LENGTH: 7
```

-continued

```
<212> TYPE: PRT
<213> ORGANISM: Artificial Sequence
<220> FEATURE:
<223> OTHER INFORMATION: Description of Artificial Sequence: designed
      peptide of the AT1 receptor

<400> SEQUENCE: 4

Gly Tyr Tyr Phe Asp Thr Asn
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: designed
      peptide of the AT1 receptor

<400> SEQUENCE: 5

Glu Asn Thr Asn Ile Thr
1               5
```